United States Patent [19]

Ishikawa et al.

[11] Patent Number: 4,532,020
[45] Date of Patent: Jul. 30, 1985

[54] PROCESS FOR PREPARING A β-(FLUOROALKYL OR FLUOROALKENYL)-β-HYDROXYALKYNE

[75] Inventors: Nobuo Ishikawa, Yokohama; Tomoya Kitazume, Tokyo, both of Japan

[73] Assignee: Daikin Kogyo Co., Ltd., Osaka, Japan

[21] Appl. No.: 586,943

[22] Filed: Mar. 7, 1984

[30] Foreign Application Priority Data

Mar. 9, 1983 [JP] Japan .................................. 58-38784
Mar. 9, 1983 [JP] Japan .................................. 58-38785

[51] Int. Cl.$^3$ .............................................. B01J 19/10
[52] U.S. Cl. ........................... 204/158 HA; 204/162 S; 204/158 S; 204/163 R; 568/812; 568/843
[58] Field of Search ........ 204/158 HA, 163 R, 158 S, 204/162 S

[56] References Cited

U.S. PATENT DOCUMENTS 4,165,269 8/1979 Castle .............................. 204/163 R Primary Examiner—Howard S. Williams
Attorney, Agent, or Firm—Armstrong, Nikaido, Marmelstein & Kubovcik

[57] ABSTRACT

A process for preparing a β-(fluoroalkyl or fluoroalkenyl)-β-hydroxyalkyne represented by the formula $$\underset{R_fCH-C\equiv CR}{\overset{OH}{|}} \qquad (I)$$

wherein $R_f$ represents a fluoroalkyl or fluoroalkenyl group and R represents an aliphatic or aromatic group, comprising reacting an alkyne represented by the formula $$R-C\equiv CH \qquad (II)$$

wherein R is the same as defined above with a fluorine containing aldehyde represented by the formula $$R_fCHO \qquad (III)$$

wherein $R_f$ is the same as defined above in the presence of catalyst under ultrasonic irradiation.

A process for preparing an α-(fluoroalkyl or fluoroalkenyl)allyl alcohol represented by the formula $$R_fCH-CH=C\underset{\diagdown R'}{\overset{\diagup R}{}} \qquad (IV)$$
$$\overset{|}{OH}$$

wherein $R_f$ represents a fluoroalkyl or fluoroalkenyl group, R represents an aliphatic or aromatic group and R' represents a hydrogen atom or an aliphatic group, comprising (1) reacting a β-(fluoroalkyl or fluoroalkenyl)-β-hydroxyalkyne represented by the formula $$\underset{R_fCH-C\equiv CR}{\overset{OH}{|}} \qquad (I)$$

wherein $R_f$ and R are respectively the same as defined above with a isobutylmagnesium halide represented by the formula $$i-C_4H_9MgX$$

wherein X represents a halogen atom, and (2) reacting the reaction mixture thus obtained above with a halide represented by the formula $$R'X'$$

wherein X' represents a halogen atom and R' is the same as defined above.

5 Claims, No Drawings

PROCESS FOR PREPARING A β-(FLUOROALKYL OR FLUOROALKENYL)-β-HYDROXYALKYNE

BACKGROUND OF THE INVENTION

1. Field of the Invention

The present invention relates to a process for preparing a β-(fluoroalkyl or fluoroalkenyl)-β-hydroxyalkyne and an α-(fluoroalkyl or fluoroalkenyl)allyl alcohol thereof.

2. Description of the Prior Art

Development of a method to introduce a trifluoromethyl group (—CF$_3$) into molecules has hitherto been one of the important subjects of study in the fluorine chemistry. There is known a process to produce a fluorine containing hydroxyalkyne by "The Chemistry of the Carbon-Carbon Triple-bond" Saul Patai (1978), published by John Wiley and Sons.

On the other hand, allyl alcohols are known as useful compounds in the synthetic chemistry. If a CF$_3$ group can be introduced into the molecule of allyl alcohols at a selected carbon and in a selected steric position, we can expect successful development of a process of synthesis of organic compounds with a CF$_3$ group introduced at an intended position.

OBJECTS AND SUMMARY OF THE INVENTION

It is an object of the present invention to provide a process for preparing a hydroxy alkyne containing a CF$_3$ group or an other fluorinated aliphatic group (hereinafter referred to as first invention).

It is another object of the invention to provide a process for preparing an allyl alcohol containing a CF$_3$ group or an other fluorinated aliphatic group at a certain position (hereinafter referred to as second invention).

To describe more specifically, the first invention provides a process for preparing a β-(fluoroalkyl or fluoroalkenyl)-β-hydroxy alkyne represented by the formula

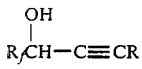  (I)

wherein R$_f$ represents a fluoroalkyl or fluoroalkenyl group and R represents an aliphatic or aromatic group, comprising reacting an alkyne represented by the formula

R—C≡CH  (II)

wherein R is the same as defined above with a fluorine containing aldehyde represented by the formula

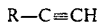  (II)

wherein R$_f$ is the same as defined above in the presence of catalyst under the ultrasonic irradiation.

According to this first invention, the target fluorinated hydroxyalkyne can be readily synthesized in a one-pot process at room temperature, since the reaction proceeds under the action of ultrasonic vibration or ultrasonic irradiation.

Compared to the conventional method for preparing the target compound comprising reacting an acetylide, which has been prepared by reacting lithium or other alkali metal with said alkyne (II) with a substrate at a low temperature, the first invention is convenient in point of reaction temperature which is usually between 20° and 50° C., preferably room temperature.

In the specification R is preferably an alkyl or alkenyl group of 1 to 10 carbon atoms, or an aromatic group. Examples of such alkyl group are a methyl, ethyl, propyl, and butyl group. Examples of such alkenyl group are a ethylene and propylene group. And an example of such aromatic group is a phenyl group. R$_f$ is preferably a fluoroalkyl or fluoroalkenyl group of 1 to 10 carbon atoms, more preferably without branching. Examples of the former are —CF$_3$, —C$_2$F$_5$, and —C$_3$F$_7$ group while examples of the latter are —C$_2$F$_3$ and —C$_3$F$_5$ group.

The catalyst can be an alkali metal, preferably sodium.

Ultrasonic irradiation can be suitably generated in an ultrasonic cleaner available in the market, for example, rated to 35 W, 32 kHz. Under action of the ultrasonic irradiation, it is possible to complete the reaction of the above alkyne and fluorinated aldehyde within from one to several hours.

An organic solvent is usually used in the reaction. Specific examples of the solvent are diethyl ether and tetrahydrofuran.

The second invention provides a process for preparing an α-(fluoroalkyl or fluoroalkenyl) allyl alcohol represented by the formula

  (IV)

wherein R' represents a hydrogen atom or an aliphatic group, R$_f$ and R are respectively the same as defined above, comprising (1) reacting said compound (I) with a isobutylmagnesium halide represented by the formula

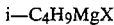

wherein X represents a halogen atom, and (2) reacting the reaction mixture thus obtained above with a halide represented by the formula

wherein X' represents a halogen atom and R' is the same as defined above.

According to the second invention, a hydroxyalkyne having a fluorinated aliphatic substituent undergoes a hydromagnesation reaction making use of i-BuMgX wherein X is the same as defined above to readily produce the target fluorinated allyl alcohol very selectively.

X in the above i-BuMgX is preferably a chlorine or bromine atom and X' in the above R'X' may be a chlorine, bromine or other halogen atom.

The above reaction of the second invention can be successfully conducted at 20° to 50° C. The solvent used therein is preferably an organic solvent, such as diethyl ether or tetrahydrofuran.

It is noted that said compound (I) used in the second invention can be synthesized by the method of first invention as already mentioned.

Other objects and aspects of the invention will become apparent from the following description of embodiments.

DESCRIPTION OF THE PREFERRED EMBODIMENTS

For example, an acetylene compound 1 and trifuluoroacetaldehyde 2, each having a general formula as given in the following reaction formula, are used as the starting materials with a catalyst metal sodium. In solvent tetrahydrofuran (THF), the reaction occurs producing the target compound 3 as follows:

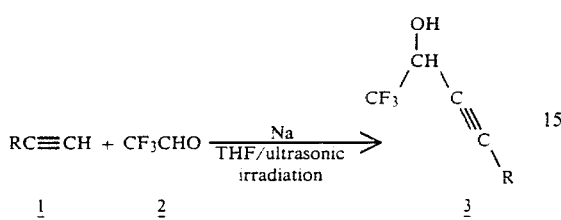

With use of a commercially available ultrasonic cleaner, the above reaction proceeds satisfactorily to give the corresponding β-(fluoroalkyl)-β-hydroxyalkyne 3 at high yield. When R in the starting material 1 was changed variously, results as shown in Table 1 were obtained.

TABLE 1

| | | Product 3 | | |
|---|---|---|---|---|
| | | | | $^{19}$F NMR* |
| R | Yield (%) | B.p. (°C./mmHg) | CF$_3$ | J(CF$_3$—CH) (Hz) |
| Methyl | 64 | 76–78/56 | 0.8 | 5.6 |
| Propyl | 68 | 78–79/35 | 1.4 | 5.6 |
| Butyl | 72 | 83–85/21 | 2.3 | 5.6 |
| Phenyl | 74 | 82/1.8 | 0.3 | 6.6 |

*External standard: CF$_3$CO$_2$H

Next, the hydromagnesation reaction to produce allyl alcohols having a CF$_3$ substituent occurs as follows.

Even with a CF$_3$ substituent in its molecule, the reactant compound, like the ordinary hydrocarbon, still undergoes the following reaction without any action of ultrasonic irradiation to selectively produce the corresponding allyl alcohol 4 in a high yield:

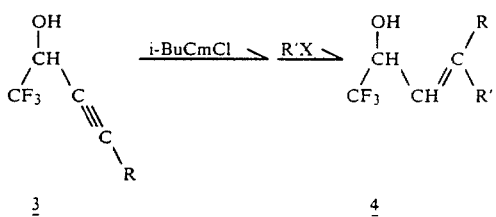

In the product 4 of the above reaction, the substituent R' is introduced at the trans position relative to the CF$_3$CH(OH) group. In this case, an important factor is that the isobutyl group of the isobutylmagnesium chloride (i-BuMgCl) is bulky and readily released. When R and R' were changed variously in the above reaction, target products corresponding to 4 were produced as in Table 2.

TABLE 2

| | | | Product 4 | | |
|---|---|---|---|---|---|
| | | Yield | B.p. | | $^{19}$F NMR* |
| R | R' | (%) | (°C./mmHg) | CF$_3$ | J(CF$_3$—CH) (Hz) |
| Butyl | H | 86 | 82–84/23 | 0.9 | 6.6 |
| Butyl | Methyl | 64 | 85–86/21 | 0.8 | 6.6 |

TABLE 2-continued

| | | | Product 4 | | |
|---|---|---|---|---|---|
| | | Yield | B.p. | | $^{19}$F NMR* |
| R | R' | (%) | (°C./mmHg) | CF$_3$ | J(CF$_3$—CH) (Hz) |
| Phenyl | H | 76 | 76–77/2 | 0.6 | 5.3 |
| Phenyl | Methyl | 61 | 84–86/2 | 0.3 | 5.3 |

Further, the following reaction gives fluorinated allyl alcohols 4a and 4b through hydroxyalkynes 3a and 3b, respectively.

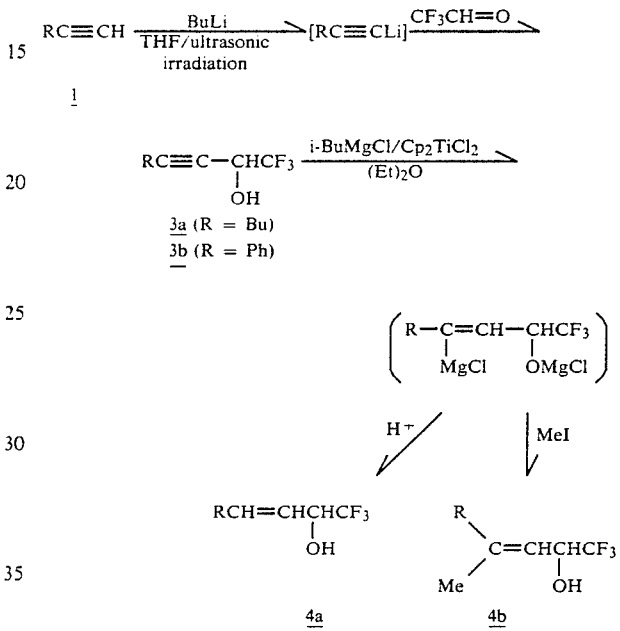

Also the above reaction gives the target products in high yield even without use of ultrasound. Products corresponding to 4a and 4b were thus obtained as in Table 3.

TABLE 3

| Product No. | R | Bp (°C./mmHg) | Yield (%) | IR (OH) (cm$^{-1}$) | $^{19}$F NMR (CF$_3$) (ppm) | Element. analysis (calcd. value) C | H |
|---|---|---|---|---|---|---|---|
| 4a | Bu | 82–84/23 | 60 | 3330 | 1.3d | 53.02 (52.74) | 7.42 (7.19) |
| 4a | Ph | 78–80/3 | 53 | 3340 | 0.3d | 59.18 (59.41) | 4.72 (4.49) |
| 4b | Bu | 82–85/21 | 72 | 3330 | 0.8d | 55.31 (55.09) | 7.86 (7.71) |
| 4b | Ph | 84–86/2 | 63 | 3335 | 0.6d | 60.96 (61.11) | 4.99 (5.13) |

Further, the following reaction also gives a different kind of hydroxyalkyne:

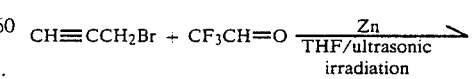

$$CF_3CHCH_2C\equiv CH$$
$$\underset{OH}{|}$$

The invention will be more clearly understood with reference to the following Examples.

EXAMPLE 1

1-hexene (6.2 g, 76 mmol) and n-butyllithium (52 ml, 1.5 M in hexane) and trifluoroacetaldehyde (7 g, 71 mmol) were reacted 3 hours under the action of ultrasonic irradiation (as generated by a commercially available ultrasonic cleaner 220H manufactured by Branson Cleaning Equipment Company). The reaction mixture was poured into aqueous 2% HCl solution and diethyl ether was used for extraction of the oily layer. The extracts were then distilled to give 1,1,1-trifluoro-3-octyne-2-ol (b.p.: 83–85° C./21 mmHg) in a yield of 72%. This hydroxyalkyne gave the following analytical data:

$^{19}$F NMR (CDCl$_3$): δ2.3 (CF$_3$, d, J$_{CF_3-CH}$=5.6 Hz).
$^{1}$H MNR (CDCl$_3$): δ0.9, 1.5, 2.3 (9H), 3.7 (OH), 4.73 (CH).

Elementary analysis: C: 53.37% (calcd. value: 53.33). H: 6.39 (calcd. value: 6.15).

EXAMPLE 2

In a solution of phenylacetylene (4.08 g, 40 mmol) in dry ether (30 ml), n-butyllithium (27 ml, 1.5 M in hexane) was slowly added at −78° C. Trifluoroacetaldehyde (3.7 g, 38 mmol) was introduced in the above mixture under bubbling and the mixture was then agitated 2 hours at −78° C. After the temperature of reaction mixture was elevated to room temperature, the whole solution was poured into aqueous 2% HCl solution. Extraction was made for the oily layer using diethyl ether. The extracts were dried on magnesium sulfate and solvent was removed. Distillation gave 1,1,1-trifluoro-4-phenyl-3-butyne-2-ol (b.p.: 82° C./1.8 mmHg) at a yield of 74%. The above product gave the following analytical data:

$^{19}$F NMR (CDCl$_3$): δ0.3 (CF$_3$, d, J$_{CF_3-CH}$=6.6 Hz).
$^{1}$H NMR (CDCl$_3$): δ3.83 (OH), 4.87 (CH, q), 7.37 (Ar—H).

Elementary analysis: C: 59.74% (calcd. value: 60.01). H: 3.86 (calcd. value: 3.53).

EXAMPLE 3

In an isobutylmagnesium chloride solution that was prepared by reacting isobutyl chloride (2.34 g, 25 mmol) and magnesium (0.66 g, 27 mmol) in dry ether (30 ml) at 0° C., dichlorobis(π-cyclopentadienyl)titanium (0.14 g, 0.56 mmol) and 1,1,1-trifluoro-4-phenyl-3-butyne-2-ol (2g, 10 mmol) were slowly added at 0° C. After 1 hour agitation at the same temperature, the reaction mixture was treated by a method similar to the one in the above Examples to obtain (Z)-1,1,1-trifluoro-4-phenyl-3-butene-2-ol (b.p.: 78°–80° C./3 mmHg) at a yield of 53%. The above product gave the following analytical data:

$^{19}$F NMR (CDCl$_3$): δ0.3 (CF$_3$, d, J$_{CF_3-CH}$=6.6 Hz).
$^{1}$H NMR (CDCl$_3$): δ4.10 (OH), 4.97 (CH, d, q, J$_{CH-CH}$=9.8 Hz), 5.83 (CH=, d, q, J$_{CH-CH}$=12 Hz), 7.0 (=CH, d).

EXAMPLE 4

In an isobutylmagnesium chloride solution that was prepared by reacting isobutyl chloride (3.74 g, 40 mmol) and magnesium (0.97 g, 40 mmol) in dry ether (40 ml) at 0° C., dichlorobis(π-cyclopentadienyl)titanium (0.22 g, 0.9 mmol) and 1,1,1-trifluoro-4-phenyl-3-butyne-2-ol (2 g, 10 mmol) were slowly added at 0° C. After 4 hour agitation of the mixture at room temperature, solvent was removed under heating for 30 min. Next, dry tetrahydrofuran (20 ml) was put into the reaction vessel and further methyl iodide (12.7 g, 90 mmol) was slowly added. After 12 hour agitation, the reaction mixture was treated by a method similar to the one in the above Examples to obtain (Z)-1,1,1-trifluoro-4-phenyl-3-pentene-2-ol (b.p.: 84°–86° C./2 mmHg) at a yield of 63%. The above product gave the following analytical data:

$^{19}$F NMR (CDCl$_3$): δ0.6 (CF$_3$, d, J$_{CF_3-CH}$=5.4 Hz).
$^{1}$H NMR (CDCl$_3$): δ2.17 (CH$_3$), 3.17 (OH), 4.47 (CH, d, q, J$_{CH-CH}$=9.4 Hz), 5.67 (CH=, d), 7.43 (Ar—H).

Reference Example

In a mixture of propargyl bromide (3.46 g, 29 mmol), zinc powder (2.3 g, 0.035 gram-atom) in tetrahydrofuran (60 ml), trifluoroacetaldehyde (1.9 g, 19 mmol) was added under bubbling. An hour later, the reaction mixture was poured into aqueous 2% HCl solution for a similar treatment to the one used in the above Examples. Distillation gave 1,1,1-trifluoro-4-pentyne-2-ol (b.p.: 95°–96° C.) at a yield of 65%. The above product gave the following analytical data:

$^{19}$F NMR (CDCl$_3$): δ3.2 (CF$_3$, d, J$_{CF_3-CH}$=6.6 Hz).
$^{1}$H NMR (CDCl$_3$): δ2.10 (CH, t, J$_{CH-CH_2}$=3 Hz), 2.57 (CH, d, d, J$_{CH-CH_2}$=7.5 Hz), 4.10 (CH, d, q), 5.37 (CH). C: 43.66% (calcd. value: 43.49). H: 3.81 (calcd. value: 3.65).

What is claimed is:

1. A process for preparing a β-(fluoroalkyl or fluoroalkenyl)-β-hydroxyalkyne represented by the formula

wherein R$_f$ represents a fluoroalkyl or fluoroalkenyl group and R represents an aliphatic or aromatic group, comprising reacting an alkyne represented by the formula

wherein R is the same as defined above with a fluorine containing aldehyde represented by the formula

wherein R$_f$ is the same as defined above in the presence of catalyst under ultrasonic irradiation.

2. A process as claimed in claim 1 wherein said ultrasonic irradiation is generated in an ultrasonic cleaner.

3. A process as claimed in claim 1 wherein said R is an aliphatic group of 1 to 10 carbon atoms, or an aromatic group.

4. A process as claimed in claim 1 wherein said R$_f$ is a fluoroalkyl or fluoroalkenyl group of 1 to 10 carbon atoms.

5. A process as claimed in claim 1 wherein said catalyst is an alkali metal.

* * * * *